United States Patent [19]
Born et al.

[11] 4,223,219
[45] Sep. 16, 1980

[54] METHOD OF AND APPARATUS FOR PRODUCING TEXTURE TOPOGRAMS

[76] Inventors: Eberhard Born, No. 19, Nederlinger Strasse, 8000 München 19; Gerald Paul, No. 24, Harbigstrasse, 8672 Selb, berfranken, both of Fed. Rep. of Germany

[21] Appl. No.: 954,254

[22] Filed: Oct. 24, 1978

[30] Foreign Application Priority Data

Oct. 28, 1977 [DE] Fed. Rep. of Germany ...... 2748501

[51] Int. Cl.$^2$ ............................................. G01N 23/20
[52] U.S. Cl. ................................... 250/272; 250/273
[58] Field of Search .............. 250/272, 273, 277 CH, 250/274, 275, 280

[56] References Cited

U.S. PATENT DOCUMENTS

| | | | |
|---|---|---|---|
| 2,500,948 | 3/1950 | Kaiser et al. | 250/277 CH |
| 3,070,693 | 12/1962 | Furnas, Jr. | 250/273 |
| 3,073,952 | 1/1963 | Rose | 250/277 CH |
| 3,852,594 | 12/1974 | Paolini | 250/272 |

*Primary Examiner*—Alfred E. Smith
*Assistant Examiner*—Thomas P. O'Hare
*Attorney, Agent, or Firm*—John C. Smith, Jr.

[57] ABSTRACT

A method of and apparatus for producing texture topograms at surface layers of non-amorphous polycrystalline bodies comprises means for producing a divergent beam of monochromatic radiation. The divergent monochromatic radiation beam is diffracted at a polycrystalline body to be examined. Slit-shaped apertures are arranged in the radiation path of the diffracted radiation and extend parallel to the diffraction plane. Means for forming an image of the picture of the diffracted radiation are arranged behind the slit-shaped apertures and at a distance from the surface of the polycrystalline body and the focussed reflex.

18 Claims, 2 Drawing Figures

METHOD OF AND APPARATUS FOR PRODUCING TEXTURE TOPOGRAMS

BACKGROUND OF THE INVENTION

This invention relates to a method of and an apparatus for producing texture topograms at surface layers of non-amorphous polycrystalline bodies.

In a polycrystalline solid body, generally the crystallites are present statistically disordered.

When on the other hand such a body is subjected to certain strains, for instance a mechanical-plastical deformation, a cooling or the like, this has the result that the crystallites previously present in the body and completely statistically distributed in their orientations are now oriented prevailingly similarly in specific directions of preference. This more or less orderly orientation of the crystallites is generally called "texture". The textures influence the technological, such as the mechanical, electrical, magnetical or the like properties of the respective polycrystalline body in the various strain directions.

For the determination of topographies, there are well-known methods, which, however, are only suited for use in connection with monocrystals. On the other hand, methods of measuring textures are also known with which it up to now, however, is not possible to produce locally differentiating texture topographies.

Presently known topographies, such as X-ray topographies, are always only produced with monocrystals and serve the purpose of reproducing interferences, such as displacements, small-angle grain borders, twins and other domains. Topography methods working strictly monochromatically with a well-defined reproduction, such as according to Lang or Berg-Barrett, in doing so use the crystal to be examined itself as monochromator. However, the angle divergence of the radiation beam to be used is permitted to be only very small, i.e. in the range of angle minutes, and this again causes an only inferior utilization of the entire radiation resulting in the radiation emitter and also long exposure times (in part many hours up to days).

Upon employment of so-called count-tube methods, for an X-ray reflex (i.e. for a reflecting lattice plane family) in a pole figure the frequency of the different layers of reflecting lattice planes within the texture preparation may be determined. In this method, however, the determination is always effected throughout a larger area of the body to be examined, and no determination is obtained on the local distribution of the crystallite orientation, i.e. on the anisotropy of the texture.

The topography method according to Lang known since long ago among the topography methods today known surely has the best resolution and the maximum contrast. The resolution suffices in order to make visible individual displacements, and it is also possible to obtain a spatial impression on the position of the displacements stereoscopically by means of two exposures at different angles of view. In the method of Lang, an X-ray beam is used which prior to its impingement upon the monocrystal to be examined passes through an aperture. The monocrystal is then adjusted in view of the beam in such a way that the wavelength of the $K\alpha_1$ radiation impinges with the Bragg angle upon the lattice plane family of the surface, the aperture in front of the monocrystal having to be provided in such a way that the angle of divergence of the radiation beam passing through the aperture is smaller than the difference to the Bragg angle of the wavelength $K\alpha_2$ which at only a slightly larger diffraction angle would furnish the same topogram, and this would have to lead to undesired superimposition. The radiation diffracted at the reflecting lattice plane family then passes through a further aperture and is exposed on a film arranged therebehind parallel to the monocrystal. In the Lang topogram, disturbed regions such as for instance displacements appear more intensely blackened than the exposure of the nondisturbed environment thereof. In the topography of Lang, only a relatively small space angle element of the emitted radiation is able to be utilized, which along with an inferior utilization of the primary beam at reflexion results in substantial exposure times in part lasting days. The use of rotary anode X-ray tubes of a high thermal load capacity does provide a shortening of the exposure time, but frequently causes difficulties with local stability of the focal spot on the rotating anode. With the Lang method, the forming of an image of texture topograms of polycrystalline bodies also is not possible with reasonable exposure times.

In contradistinction to the Lang method wherein only the $K\alpha_1$ radiation is used for forming an image, which thus represents a strictly monochromatic method, in the method of Berg-Barrett generally this separation is dispensed with, a certain inferiority of well-definedness awarely being accepted. Like all partially monochromatical methods, the image contains a substrate blackening which is caused by the diffraction of the retarding continuum. The Berg-Barrett method works with a simple reflexion method: The radiation of a certain wavelength $K\alpha$ emitting from the line focus of the X-ray tube is reflected upon a film, provided it is incident upon the monocrystal to be examined respectively at the Bragg angle. The image in the diffraction plane is well-defined and length-true, but in the plane normal thereof, an enlargement is effected, the overall image thereby being distorted. A condition for a well-defined image there is the use of only one wavelength, the monochromatisation being achieved at the monocrystal examined itself—similar to the method of Lang. The Berg-Barrett method requires a comparatively only low apparatus expense and also has shortened exposure times as compared with the method of Lang.

Focussing X-ray methods are also known (e.g. those of Seemann and Bohlin), wherein in setting out from a divergent beam of X-rays the origine of which is on the same circle as the crystal powder preparation to be examined the diffracted radiation is focussed back to a point of this circle. When a diffraction arrangement of Seemann-Bohlin is combined with a curved monochromator (e.g. Johansson-Monochromator), thereby the X-ray diffraction method of Guinier is made possible. This method is characterized in that it is strictly monochromatical and focussing. The strict monochromasy permits long exposure times and thus next to the measurement of strong also that of very weak intensities upon suppression of retarding radiation and interfering lines from the own spectrum of the tube.

In order to determine the texture of a polycrystalline body, texture measurement methods have become known which set out from a focussing according to Bragg-Brentano. This measurement methods result in the recording of a pole figure from which predominant textures are able to be noted, but in which a locally differentiated topography of the body to be examined is not perceivable.

SUMMARY OF THE INVENTION

In setting out therefrom, the invention is based on the problem of improving a method of the prior art nature and an apparatus for performing the method to the extent that locally differentiating texture topographies are able to be produced in utilizing a substantially higher primary beam intensity with reasonable exposure times.

According to the present invention, this problem is solved by a method of producing texture topograms at surface layers of non-amorphous polycrystalline bodies in adaptation of the conventional Guinier method, wherein a divergent beam of monochromatic radiation is diffracted at a polycrystalline body in a diffraction plane and the diffracted radiation is focussed into a reflex on a focussing circle, comprising the steps of (a) masking out a radiation beam only slightly diverging normal of the diffraction plane from the diffraction cone of the diffracted radiation for forming an image, and (b) using the diffracted radiation for forming the image or a registration at a distance from the focussed reflex and from the body.

Preferably, the forming of an image is effected on a radiation-sensitive film layer, again advantageously the forming of the image being effected parallel to the surface layer of the body.

Preferably, in the method of this invention the spacing of the image from the body is selected to be twice as large as the distance between the body and the focussed reflex, the image resulting being produced congruent and as a non-mirror image relative to the texture of the body to be examined.

The masking of the radiation beam is effected preferably by means of slit-shaped apertures (so-called "Soller slits") arranged parallel to the diffraction plane between the body and the image locus.

As radiation, X-ray beams are preferably used. Since because of the comparatively small area extension of an X-ray anode without screening only relatively small material samples are able to be examined, it is furthermore advisable to move the material sample and the film relative to the system of X-ray tube, monochromator and slit apertures in such a way that the monochromatic X-ray radiation beam scans the sample generally screen-like, the individual images being re-composed on the film. This can be achieved in that with a stationary arrangement of the Soller slits the body and the image-forming means are moved with the same velocity relative to the Soller slits normal of the diffraction plane. Thereby, it is at the same time avoided that the metal sheets of the Soller slits form images as shades. For an enlargement of the surface area capable of forming an image, it moreover is advisable to move the body and the film anti-parallel relative to one another with a suitable velocity within the diffraction plane.

In this context, the film and the sample may for instance be moved in countersense with the same velocity, and the radiation source as well as the slit apertures may be stationary, however, a converse kinematic arrangement may also be provided.

For a monochromatisation of the X-ray radiation, the use of a bent crystal monochromator is recommended.

As divergence for the beam of monochromatic radiation, an angular range of 2° to 4° is recommended, since in this divergence range an optimalization is achievable between the utilization of the X-ray radiation and the avoidance of undesired fringe radiation focus insufficiencies.

In the apparatus according to the invention, the above defined problem is solved in that in the radiation path of the diffracted radiation parallel to the diffraction plane slit-shaped apertures ("Soller slits") are arranged and therebehind at a distance from the surface of the polycrystalline body and the focussed reflex means are arranged for forming an image of the picture of the diffracted radiation.

The means for producing the divergent beam of monochromatic radiation preferably comprise an X-ray tube and a crystal monochromator for the monochromatisation of the radiation of the X-ray tube. As a crystal monochromator, preferably a bent crystal monochromator is utilized, in particular one of the Johansson type.

Advantageously, the slit-shaped apertures are arranged parallel to the diffraction plane and between the body to be examined and the image-forming means. In an advantageous development of the apparatus according to the invention, for focussing the diffracted radiation, the line focus of an X-ray tube is provided, the height of the slit-shaped apertures corresponding to the length of the line focus.

Advantageously, the body and the means on which an image is formed are movable with the same velocity relative to the arrangement comprising the monochromator and the slit-shaped apertures normal of the diffraction plane. A screening of the surface of the body to be examined in a direction normal thereof can be achieved in that the body and the means on which the image is formed are movable anti-parallel relative to one another within the diffraction plane. The velocities of the anti-parallel movement directed opposite to one another of the body and the image-forming means are then to be selected in such a way that the ratio thereof corresponds to the ratio of the respective distances of the respective moved part (body or image-forming means) from the focussed reflex.

The method and the apparatus according to the invention permit a production of locally differentiating texture topograms in employing a reasonable apparatus expense. At the same time, it is possible to use a substantially greater diverging monochromatic X-ray beam for diffraction than was permitted up to now with the topography methods known up to now. Thereby, a primary beam intensity increased in order may be achieved and utilized.

The method of this invention moreover permits to vary the penetration depths of the radiations into the sample body respectively by a wavelength of the radiation selected differently from measurement to measurement and to thereby for instance determine to what extent a texture or a texture fault extends into the depth of the body. The relatively low apparatus expense required also permits to construe the apparatus according to the invention transportable, it thereby for instance being employable for the testing of airplane prototypes at particularly neuralgic points and merely a cleaning of the sample site to be tested is required, but not the dismantling thereof.

The method and the apparatus according to this invention may be used within a broad range of use: This range of use extends for instance from quality control for the production of objects to falsification or crime fighting, for instance the determination of ground-away chassis serial numbers in automotive vehicles or the location of coin falsifications (overcoinings, grindings etc.). The possibility of producing locally differentiated texture topograms offered by the invention finally makes available to extensive areas of engineering an instrument needed since long, the cost of which is in a very reasonable order in consideration of economical aspects.

BRIEF DESCRIPTION OF THE DRAWINGS

The invention will now be described by way of example and with reference to the accompanying drawings in which.

DESCRIPTION OF THE PREFERRED EMBODIMENTS

Figure 1:
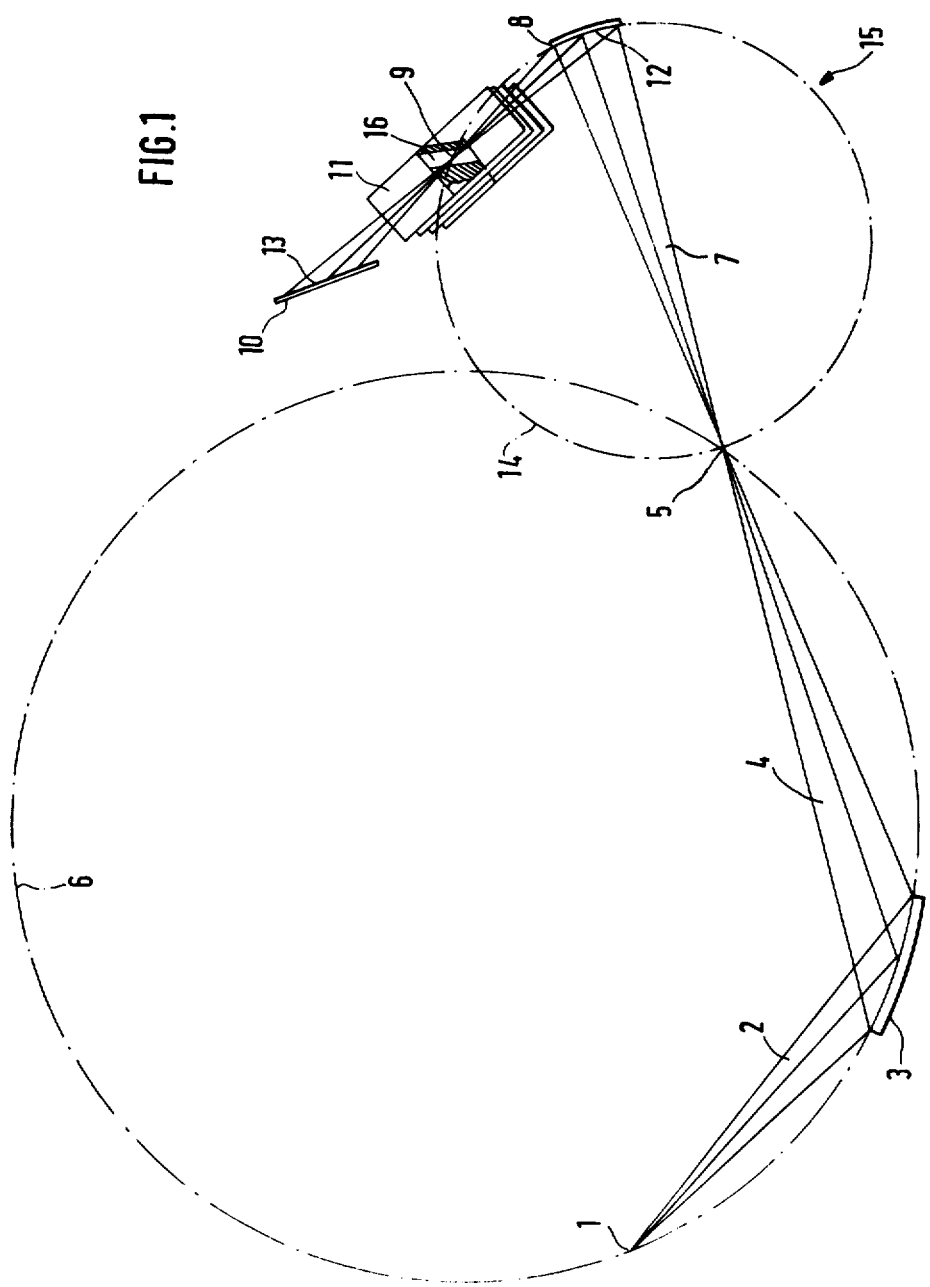
FIG. 1 is a semi-diagrammatic illustration of the method according to the invention.

FIG. 1 shows a radiation source 1 which emits a divergent polychromatic radiation beam 2. This beam strikes upon a bent crystal monochromator 3 which emits a convergent beam of monochromatic radiation 4 focussed at the position of the focal line 5. The radiation source 1, the monochromator 3 and the focal line 5 are disposed on the focussing circle 6 of the monochromator means.

Behind the focal line 5, the initially convergent radiation beam emitted by the monochromator 3 now turns into a divergent beam 7 of monochromatic radiation which strikes upon the surface 12 of the polycrystalline body 8 or a preparation to be tested. The radiation diffracted at the reflecting lattice planes of the body 8 is diffracted on a cone shell coaxial to the primary beam because of the variety of possible positions of the individual crystallites of the body to be examined. From this cone shell, by means of an aperture system of Soller slits 11 parallel to the diffraction plane (arranged between preparation and film 10) a radiation beam only very slightly divergent normal of the diffraction plane is screened out which then strikes upon an image-forming or registration means 10.

The position of the Soller slits 11 may be anywhere between the image-forming or registration means and the body. The radiation beam diffracted at the body 8 is focussed to a reflex 9, which together with the body 8 and the focal line 5 is disposed on the focussing circle 14 of the diffraction arrangement 15. The reflex 9 need not necessarily be defined within the Soller slits, rather the Soller slits also may be disposed such that the reflex 9 defines outside of them. For warding off other still present Bragg reflexes from the image-forming means, it is advisable to mask off the reflex 9 used for the image-forming by a further aperture 16 defined by a narrow slit normal of the Soller slits 11, i.e. to provide for that only this reflex is permitted to pass and other further present Bragg reflexes are warded off from forming an image on the film 10. This further aperture 16 is only illustrated basically in FIG. 1 as well as in FIG. 2.

On the image-forming means 10, by the diffracted radiation an image 13 is caused which represents the desired texture topogram.

As image-forming means 10 preferably suitable radiation-sensitive films may be used. There is also the possibility, however, to employ here some other suitable means instead of a film, for instance a counting tube or some other registration means. The position of the image-forming means 10 may be adjusted to conform to the conditions of the respective instance at hand. It is not even required that the reflex is defined between the body 8 to be examined and the image-forming means 10, rather, in case this should be required, the image-forming means 10 also may be arranged between the focussed reflex 9 and the body 8 to be examined. When, as illustrated in the drawings, a film 10 is selected as image-forming means, the position of which is aligned parallel to the position of the body 8 to be examined and the distance of which to the focussed reflex 9 is equal to the distance between the body 8 and the reflex 9, then the image 13 thereby resulting is congruent to the area of the surface 12 of the body 8 covered by the radiation, thus no mirror-image. The height of the slit-shaped apertures 11 is selected as high to advantage as the length of the line focus of the X-ray tube 1.

Figure 2:
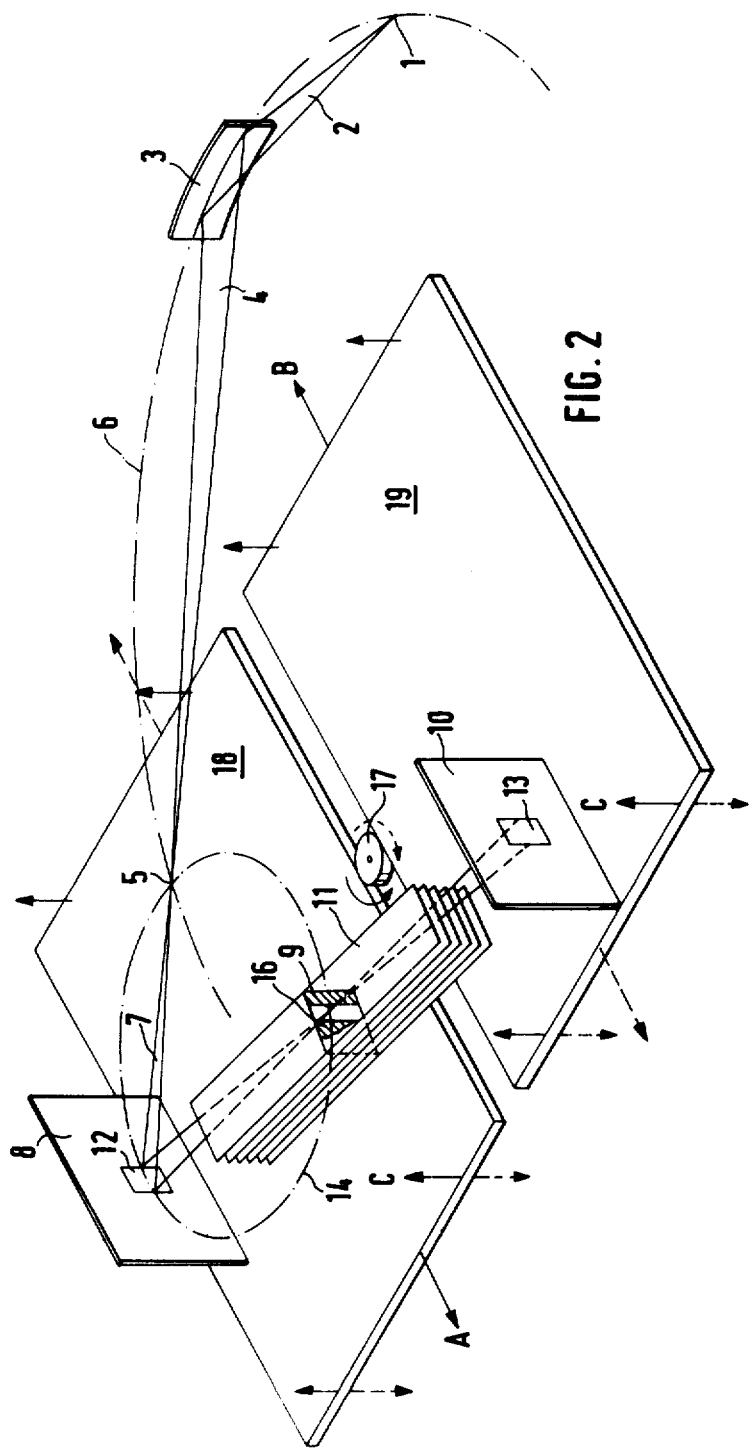
FIG. 2 is a perspective fundamental illustration of an apparatus according to the invention.

The relative small area extension of the X-ray anode has the result that also only relatively small material samples at the body 8 could be examined. In order to be able to cover a larger area of the surface 12 of the body 8, it is of an advantage when a screen-like scanning of the surface 12 of the body 8 is effected, the individual images of which are then re-composed finally on the film again. Such a screening is performed preferably in two planes, i.e. within the diffraction plane and normal thereof. This can be achieved in that the Soller slits are arranged stationary and the body 8 to be examined as well as the image-forming means 10 are moved with the same velocity relative to the Soller slits normal of the diffraction plane up and down. Thereby at the same time the forming of an image of the Soller slits as a shade on the film can be avoided. Furthermore, the screening is moved normal thereof to the body 8 to be examined and to the film 10 anti-parallel, i.e. opposite parallel relative to one another with suitable velocities within the diffraction plane, like this for instance possible by the arrangement of a wheel 17 illustrated in FIG. 2: There a carrier plate 18 for the body 8 to be examined and a carrier plate 19 for the image-forming means are respectively in friction engagement with a wheel 17, whereby upon a movement for instance of the carrier plate 18 in direction of the arrow A an opposite parallel movement of the carrier plate 19 in direction of the arrow B (and vice versa) is caused. The carrier plates 18 and 19 shown in FIG. 2 are additionally at the same time, and also in the same sense with the same velocity, moved normal of the lateral movement upwardly (direction of the arrows C) and conversely. The velocities of movement of the carrier plates 18 and 19 upwardly or downwardly on the one hand and normal thereof laterally on the other hand therefore are to respectively be correlated in such a way that a complete screening of the entire body 8 to be examined can be effected without any omission of any local areas. This means that in the practical instance e.g. a relatively slow movement upwardly as compared with a much quicker movement relative thereto laterally is selected or vice versa. So for instance for a completed cycle of movements upwardly and back again a period of time of about 30 minutes may be selected, while the movement directed laterally thereof is associated with a forward and backward cycle of then only a few minutes. The cycle times to be selected may respectively be conformed to the instance of use individually, as suited.

The basical detail illustration of a section of an apparatus according to the invention shown in FIG. 2 again shows the line focus of an X-ray tube from which the convergent radiation beam of polychromatic light strikes upon the bent crystal monochromator 3 from which an initially convergent beam 4 of monochromatic radiation is reflected and focussed in the point 5 of the focussing circle 6 of the monochromator 3. From there a divergent beam 7 of monochromatic radiation is emitted to the surface 12 of the preparation (body) 8 to be examined which is attached to the carrier plate 18. The diffracted radiation emitted from this preparation is focussed on the focussing circle 14 of the diffraction arrangement into a reflex 9 and subsequently forms an image on the image-forming means 10 (film) within an area 13. Between the preparation and the film 10, there is provided an arrangement of Soller slits 11, the slits of which are positioned parallel to the diffraction plane. The height of the stack of Soller slits 11 should at least correspond to the length of the line focus of the X-ray anode. In the illustrated apparatus, the distance between the preparation 8 and the focussed reflex 9 is equal to the distance between the reflex 9 and the film 10 so that the image formed on the film 10 is congruent to the area of the preparation of which an image is formed.

In contradistinction to the already indicated movability of the carrier plates 18 and 19 as well as the body 8 and the film 10 connected thereto, the arrangement of the Soller slits 11 just as well as that of the monochromator 3 and the focal line of the X-ray anode is stationary, i.e. the Soller slits 11 are not rigidly connected to the carrier plate 18 or 19.

The invention may be embodied in other specific forms without departing from the spirit or the essential characteristics thereof. The embodiments are therefore to be considered in all respects as illustrative and not restrictive.

What is claimed is:

1. A method of producing texture topograms at surface layers of non-amorphous polycrystalline bodies in adaptation of the conventional Guinier method, wherein a divergent beam of monochromatic penetrating radiation is diffracted at the surface of a polycrystalline body in a diffraction plane and the diffracted radiation is focussed into a reflex on a focussing circle, comprising the steps of
    (a) masking out by means of Soller slits a radiation beam only slightly diverging normal of the diffraction plane from the diffraction cone of the diffracted radiation for forming an image, the Soller slits being arranged parallel to the diffraction plane between the body and the image, and
    (b) using the diffracted radiation for forming the image or a registration at a distance from the focussed reflex and from the body.

2. A method according to claim 1, wherein the image is formed on a radiation-sensitive film layer.

3. A method according to claim 1, wherein the image is formed parallel to the surface of the body.

4. A method according to claim 1, wherein the distance of the image from the body is twice as great as the distance between the body and the focussed reflex.

5. A method according to claim 1, wherein the body and the means on which the image is formed or a registration is effected are moved with the same velocity anti-parallel relative to one another within the diffraction plane.

6. A method according to claim 1, wherein for a stationary arrangement of the Soller slits the body and the means on which the image is formed or a registration is effected are moved with the same velocity relative to the Soller slits normal of the diffraction plane.

7. A method according to claim 1, wherein X-ray radiation is used as radiation.

8. A method according to claim 7, wherein a bent crystal monochromator is used for effecting monochromatisation of the X-ray radiation.

9. A method according to claim 1, wherein the divergence of the beam of monochromatic radiation is 2° to 4°.

10. An apparatus for producing texture topograms at surface layers of non-amorphous polycrystalline bodies, comprising
    (a) means for producing and directing a divergent beam of monochromatic penetrating radiation along a path;
    (b) means for supporting a polycrystalline body, a surface of which is to be examined, in a position in said path such that the surface of said body will diffract the divergent monochromatic radiation beam in a diffraction plane to provide a diffracted radiation focussed to a reflex;
    (c) Soller slit means defining a plurality of slit-shaped apertures arranged in the path of the diffracted radiation and extending parallel to the diffraction plane; and
    (d) means for forming an image of the picture of the diffracted radiation and arranged in the path of the diffracted radiation downstream of said Soller slit means and at a distance from said surface of the polycrystalline body and said focussed reflex.

11. An apparatus according to claim 9, wherein said means for producing the divergent beam of monochromatic radiation comprises an X-ray tube and a crystal monochromator for monochromatisation of the radiation of the X-ray tube.

12. An apparatus according to claim 11, wherein said crystal monochromator comprises a bent crystal monochromator.

13. An apparatus according to claim 12, wherein the bent crystal monochromator is one of the Johansson type.

14. An apparatus according to claim 10, wherein for focussing the diffracted radiation the line focus of an X-ray tube is provided and the height of the slit-shaped apertures corresponds to the length of the line focus.

15. An apparatus according to claim 11, further comprising means for moving the body and the means for forming an image with the same velocity relative to the arrangement comprising the monochromator and the Soller slit means normal of the diffraction plane.

16. An apparatus according to claim 15, further comprising means for moving the body and the means for forming an image anti-parallel relative to one another within the diffraction plane.

17. A method according to claim 1 wherein said diffracted radiation is passed through mask means defining a narrow slit normal to the slits of the Soller slit means to permit only said reflex to pass therethrough and prevent any further reflexes from forming an image.

18. An apparatus according to claim 10 further comprising mask means defining a narrow slit normal to the slit of said Soller slit means and arranged in the path of the diffracted radiation to permit only said reflex to pass therethrough and prevent any further reflexes from forming an image on said means for forming an image.

* * * * *